United States Patent [19]

Sandulyak et al.

[11] Patent Number: 4,492,921
[45] Date of Patent: Jan. 8, 1985

[54] METHOD OF DETERMINING THE QUANTITY OF SOLID FRACTION OF FERROMAGNETIC MATTER IN A FLUID

[75] Inventors: Alexandr V. Sandulyak; Vyacheslav I. Garaschenko; Oleg J. Korkhov, Rovno, all of U.S.S.R.

[73] Assignee: Ukrainsky Institut Inzhenerov Vodnogo Khozyaistva, Leninskaya, U.S.S.R.

[21] Appl. No.: 482,453

[22] Filed: Apr. 6, 1983

[51] Int. Cl.³ .............................................. G01N 15/06
[52] U.S. Cl. ..................................... 324/204; 73/61 R
[58] Field of Search ................. 324/204; 73/61 R, 53, 73/432 PS; 209/213, 215, 225

[56] References Cited

U.S. PATENT DOCUMENTS

| 3,334,516 | 8/1967 | Cedrone | 73/61 R |
| 3,505,876 | 4/1970 | Niebergall | 73/61 R X |
| 3,686,926 | 8/1972 | Miller et al. | 73/61 R |
| 4,020,676 | 5/1977 | Nuxhall et al. | 73/61 R |

FOREIGN PATENT DOCUMENTS 274492  9/1970  U.S.S.R. ............................. 73/61 R

OTHER PUBLICATIONS

"Determining Magnetic Forms Of Iron Compounds In Water Of Electric Power Stations" by A. V. Sandulyak et al., Published in vol. 9 of the Izvestia Vuzov SSSR—Energetika, 1979 w/ Translation.

Primary Examiner—Howard A. Birmiel
Assistant Examiner—Joseph W. Roskos
Attorney, Agent, or Firm—Fleit, Jacobson, Cohn & Price

[57] ABSTRACT

A predetermined quantity of the fluid to be analyzed is made to pass through magnetized filtering packing, and the content of the solid fraction is measured after the exit of the fluid from the packing, before its re-entry into it. Recirculation is continued until a permanent, unvarying residual content of the solid phase in the fluid is attained. The fluid subjected to the recirculation is periodically acted upon by an alternating magnetic field, outside the packing.

3 Claims, 3 Drawing Figures

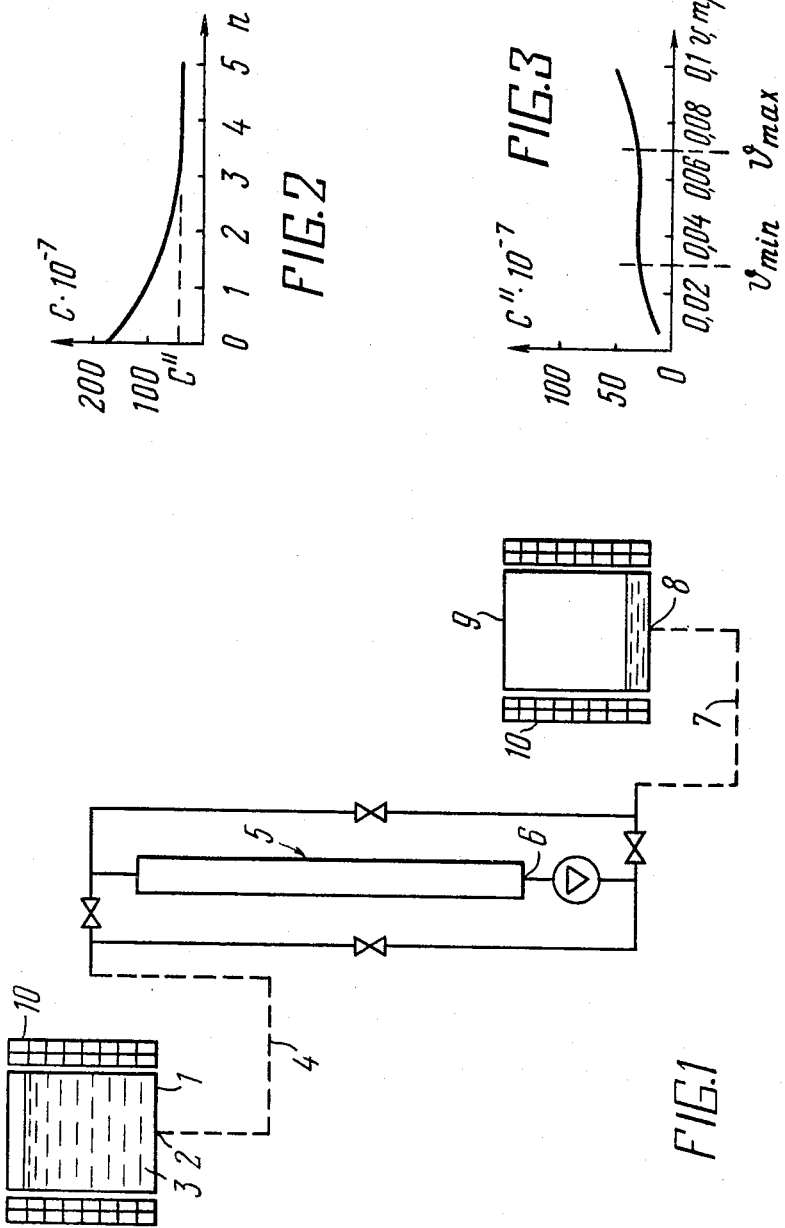

METHOD OF DETERMINING THE QUANTITY OF SOLID FRACTION OF FERROMAGNETIC MATTER IN A FLUID

FIELD OF THE INVENTION

The invention relates to magnetic separation of materials, and more particularly it relates to a method of determining the quantity of a solid fraction of ferromagnetic matter in a fluid, and can be utilized in the chemical and general engineering, in steam power generation, in metallurgy and in other industries and technologies where the quantity and percentage of the ferromagnetic fraction of solid inclusions, e.g. iron-containing impurities, is to be evaluated in a fluid, e.g. liquefied ammonia, ammonia water, an alkali, a condensate, recirculation water, lubrication oil, and the like.

BACKGROUND OF THE INVENTION

The content of ferromagnetic fraction or phase in many cases is to be determined to give the answer to the problem of advisability of using in a certain technology magnetic separators of the kinds widely utilized in various industries, and also to assess the expected efficiency of their performance. In such cases, the availability of veritable information on the quantity and percentage of the ferromagnetic fraction of the solid inclusions enables to give in advance an adequately accurate answer on whether the separator is going to operate efficiently, and whether its incorporation is feasible or not. By having made trustworthy measurements of the quantity and percentage of ferromagnetic solid phase at various points and in various streams of the production process flow, it is also possible to draft an optimized, efficient and economic design of installing the magnetic separator at minimum cost and with time saved.

There are known various methods of determining the quantity of the solid fraction or phase of ferromagnetic matter in a fluid, based on the principle of magnetic separation of solid particles carried by the fluid. Thus, in an article titled "Determining Magnetic Forms of Iron Compounds in Water of Electric Power Stations" by A. V. Sandulyak et al. published in Vol. 9 of the "Izvestia Vuzov SSSR-Energetika" scientific and technical magazine, 1979, there is described an approximation method including taking a sample of a predetermined volume of a fluid to be analyzed, carrying iron-containing impurities, ferromagnetic ones included, recirculating it through magnetized ferromagnetic packing and measuring the content in the fluid, after its passage through the packing and before its re-entry (and also prior to the recirculation), of every iron-containing impurity, e.g. by the sulphosalicylate or ortophenanthronile technique, the recirculation being continued until unvariable or permanent content of the iron-containing impurities is attained. Then the content of the ferromagnetic matter is found by subtraction of the found quantity of the residual content of iron-containing impurities from the initial content of these impurities.

A shortcoming of this method is the fact that, although offering a higher accuracy then another known "magnetic" method (e.g. by separation over a permanent magnet, or else separation in a wedge-shaped magnetic gap), the method is not proof against errors developing when the optimized flow velocity duty is not strictly observed, and also when there are not ensured conditions precluding unwanted, in this case, aggregation (or flocculation) of the particles that have passed through the zone of magnetic action. What concerns the abovementioned flow velocity duty, the probable error of the known method may be caused by the fact that with relatively low filtration velocities, non-ferromagnetic particles tend to settle alongside of ferromagnetic ones, thus stepping up the obtained value of the ferromagnetic fraction of the particles. And vice versa, with relatively high filtration velocities some turbulence develops in the pores of the packing, affecting the magnetic settling of ferromagnetic particles and, besides, resulting in some particles that have already settled being carried away, whereby the obtained value becomes unduly low.

SUMMARY OF THE INVENTION

It is an object of the present invention to create a method of determining the quantity and percentage of the ferromagnetic phase or fraction in a fluid, which should provide for obtaining stable results characteristic of the true quantity and, hence, percentage of the solid fraction or phase of the ferromagnetic matter in the fluid, and should give grounds for veritably assessing the expected effectiveness of the performance of magnetic separators and, thus, the feasibility of their installation.

These and other objects are attained by a method of determining the quantity of the solid phase or fraction of ferromagnetic matter in a fluid, including recirculating a predetermined volume of the fluid under analysis through magnetized filtering packing, measuring the content of the solid fraction of the matter before the re-entry of the fluid into the filtering packing, after its exit therefrom, and continuing the recirculation until the permanent residual content of the solid fraction is attained, used for the evaluation of the initial content thereof, in which method, in accordance with the present invention, the fluid subjected through recirculation through the filtering packing is periodically acted upon by an attenuating alternating magnetic field outside the packing, to demagnetize the particles of the solid fraction of the matter, remaining in the fluid. This recirculation may be performed with different portions of the fluid under analysis having the same volume and composition, varying the filtering rate from one portion to another one, the successive changes of the portions being continued until a stable value of the residual content of the solid fraction of the matter in the fluid is attained, independent from the filtering rate.

The advantage of the invention arises from the fact that by subjecting to cyclic magnetic filtering a succession of portions of the fluid at different filtering rates or velocities from portion to portion, there is attained such an outcome when the measured quantity of the solid fraction or phase of the impurities in the fluid becomes stable irrespectively of the filtering rate (within a certain range of the filtering rates, limited both from above and from below). With the fluid being subjected to the action of an attenuating alternating magnetic field between its exit from the packing and its entering the packing once again (to demagnetize the particles and prevent their flocculation), the outcome obtained is a true reflection of the actual content of the solid fraction of ferromagnetic matter in the fluid.

It is expedient that the method should be performed in a range of filtering rates or velocities from 0.03 m/s to 0.07 m/s, i.e. in the range where, on the one hand, unwanted mechanical settling of non-ferromagnetic particles at the packing is already eliminated, while, on the other hand, a turbulent duty of the flow of the fluid through the pores of the packing has not yet developed sufficiently to affect the magnetic settling of ferromagnetic particles at the packing.

SUMMARY OF THE DRAWINGS

The present invention will be further described in connection with examples of performing the disclosed method, meant to illustrate but not to limit the present invention, and with appended drawings, wherein:

FIG. 1 is a schematic block diagram of an apparatus capable of performing the method of determining the quantity of the solid fraction of ferromagnetic matter in a fluid, according to the invention;

FIG. 2 illustrates the results of measuring the concentration C of iron prior to the cyclic magnetic filtering and after each one of the five cycles of filtering one portion of a condensate, with the filtering rate $V = 0.04$ m/s, until the permanent residual content of concentration $C''$ of iron is attained (with the number of the filtering cycles $n \geq 3$);

FIG. 3 illustrates the data on the residual content or concentration $C''$ of iron, obtained experimentally with a series of similar portions of the condensate, similarly with FIG. 1, but with different filtering rates V.

DESCRIPTION OF EMBODIMENT OF THE INVENTION

The disclosed method is performed, as follows. A vessel 1 having a volume of 5 to 10 liters, e.g. a glass one, having an outlet 2 in its bottom is filled through the neck with a portion of the fluid 3 to be analyzed, and iron concentration in the fluid is measured by any suitable known method, e.g. the sulphosalicylate, ortophenanthroline, or other similar technique. Then the vessel 1 is raised to a height providing the necessary hydrostatic head and connected via a line 4, e.g. a length of rubber hose, with a laboratory-type magnetic separator 5, e.g. including a tubular chamber filled internally with ferromagnetic, by all means non-corroding filtering packing or checkerwork (e.g. spheres, shavings or the like—not shown) and positioned internally of a solenoid (not shown, either) connected to a d.c. power supply. The outlet 6 of the magnetic separator 5 is connected via a line 7 with the bottom outlet of a vessel 9 similar to the one mentioned above. Then the fluid is let to flow by gravity into this second vessel 9 through the laboratory-type magnetic separator 5 at a predetermined rate or velocity V. Once filled with the fluid, the second vessel 9 is subjected to the action of an attenuating magnetic field, e.g. using a solenoid 10 for the purpose. Following this first filtering cycle and measuring once again the concentration of iron, there are performed the second, third and other successive similar cycles, until the residual concentration $C''$ of iron is obtained, which is permanent and depends no longer either on the number of the filtering cycles, or on the filtering rate or velocity, which is illustrated in FIG. 2.

Upon having determined by experiment one relationship or curve, of the kind shown in FIG. 2, and the first value $C_1''$ corresponding to the filtering rate $V_1$, the first portion of the fluid is poured away, the vessels, lines and separator are flushed, and the first vessel 1 is filled once again with a similar portion of the fluid, and the abovedescribed process is repeated in exactly the same way, but with a different filtering rate or velocity $V_2$, until the second curve is experimentally found, similar to the one illustrated in FIG. 2, and the second value $C_2''$ is obtained. The same technique is used to obtain $C_3''$ corresponding to $V_3$, $C_4''$ corresponding to $V_4$, $C_5''$ corresponding to $V_5$, and so on. These values are used to plot the curve of dependence of the value of residual concentration $C''$ on the filtering rate (FIG. 3), and thus to determine the range of filtering rates V (from $V_{min}$ to $V_{max}$) within which the value of $C''$ is practically unvarying. This range of rates V is set down as the working one.

However, conducting numerous tests with numerous portions of a fluid may be avoided by performing the filtering process at one and the same velocity selected from the range from 0.03 to 0.07 m/s. Then, in order to obtain the desired value $C'$, it will be sufficient to determine experimentally but a single relationship or curve of the kind illustrated in FIG. 2.

The concentration $C'$ of the ferromagnetic fraction of iron-containing impurities is found by subtraction of the concentration $C''$ of non-ferromagnetic fraction of the impurities from the initial concentration C of the impurities. The experiments illustrated in FIG. 2 yielded the following value of $C':C' = 115.10^{-7}$, and the ratio or percentage of the ferromagnetic fraction of the impurities to their total amount (C':C) equals: $C':C = 0.72:1$.

Numerous modifications and changes may be introduced into the embodiment described hereinabove without departing from the scope and spirit of the invention, as defined by the appended claims.

What we claim is:

1. A method of measuring the quantity of the solid fraction of ferromagnetic matter in a fluid, including recirculating a predetermined volume of the fluid to be analyzed through magnetized filtering packing, acting periodically upon said fluid subjected to recirculation through the magnetized packing by an attenuating magnetic field outside the magnetized packing, to demagnetize the particles of the solid fraction remaining in the fluid, measuring the content in said fluid of the solid fraction of the material between its exit from the packing and successive re-entry into the packing, and continuing said recirculation until a permanent residual content of the solid fraction in said fluid is attained, used to evaluate the initial content thereof.

2. A method as set forth in claim 1, wherein said recirculation is conducted with different portions of said fluid to be analyzed having the same volume and composition, varying the filtering rate from portion to portion, the successive changes of the portions being continued until a stable value of the residual content of the solid fraction of the matter in said fluid is attained, independent from the filtering rate.

3. A method as set forth in claim 1, wherein the filtering rate is within a range from 0.03 m/s to 0.07 m/s.

* * * * *